United States Patent [19]

Metzger et al.

[11] 4,195,181
[45] Mar. 25, 1980

[54] 1,3,4-THIADIAZOLE COMPOUNDS AND HERBICIDAL COMPOSITIONS

[75] Inventors: Carl Metzger, Wuppertal; Ludwig Eue; Robert R. Schmidt, both of Cologne, all of Fed. Rep. of Germany

[73] Assignee: Bayer Aktiengesellschaft, Leverkusen, Fed. Rep. of Germany

[21] Appl. No.: 771,729

[22] Filed: Feb. 24, 1977

Related U.S. Application Data

[63] Continuation of Ser. No. 433,604, Jan. 15, 1974, abandoned.

[30] Foreign Application Priority Data

Jan. 23, 1973 [DE] Fed. Rep. of Germany ....... 2303079

[51] Int. Cl.² .................... A01N 9/12; C07D 417/04
[52] U.S. Cl. .................... 544/316; 548/137; 71/90
[58] Field of Search ............. 71/90; 260/256.5 R, 260/306.8 D; 544/316

[56] References Cited

U.S. PATENT DOCUMENTS

| | | | |
|---|---|---|---|
| 3,925,403 | 12/1975 | Krenzer | 71/90 |
| 3,932,410 | 1/1976 | Krenzer | 260/256.5 R |
| 3,979,388 | 9/1976 | Krenzer | 260/256.5 R |
| 4,006,009 | 2/1977 | Krenzer | 71/90 |
| 4,028,375 | 6/1977 | Krenzer | 260/306.8 D |

Primary Examiner—Alton D. Rollins
Assistant Examiner—Lisa Jones
Attorney, Agent, or Firm—Sprung, Felfe, Horn, Lynch & Kramer

[57] ABSTRACT

New heterocyclic-substituted 1,3,4,-thiadiazole derivatives of the formula

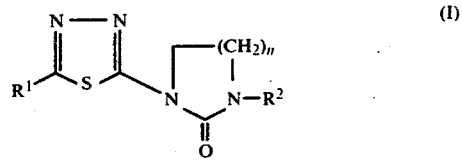

in which
  $R^1$ is alkyl, alkenyl, haloalkyl, optionally substituted aralkyl, optionally substituted aryl, alkylthio, alkylsulfonyl, alkylsulfoxyl, aralkylthio, aralkylsulfonyl or aralkylsulfoxyl,
  $R^2$ is methyl or ethyl, and
  n is 1 or 2, are surprisingly effective as herbicides and are particularly useful as selective herbicides for combating grasses, especially in crops of cereals or cotton.

4 Claims, No Drawings

1,3,4-THIADIAZOLE COMPOUNDS AND HERBICIDAL COMPOSITIONS

This is a continuation, of application Ser. No. 433,604, filed Jan. 15, 1974 now abandoned.

The present invention relates to certain new heterocyclic-substituted 1,3,4-thiadiazole compounds, to herbicidal compositions containing them and to their use as herbicides.

It is known from German Offenlegungsschrift (German Published Specification) 1,795,117 that imidazolidin-2-ones, especially imidazolidin-2-one-carboxylic acid isobutylamide, can be used for combating weeds. However, their action against grasses, for example varieties of Echinochloa and Lolium, is not always satisfactory, especially if low amounts and concentrations are used.

The present invention provides heterocyclic-substituted 1,3,4-thiadiazole derivatives of the formula

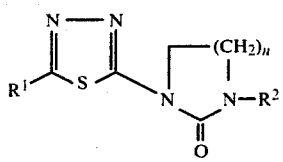

in which
R$^1$ is alkyl, alkenyl, haloalkyl, optionally substituted aralkyl, optionally substituted aryl, alkylthio, alkylsulfonyl, alkylsulfoxyl, aralkylthio, aralkylsulfonyl or aralkylsulfoxyl,
R$^2$ is methyl or ethyl, and
n is 1 or 2.

Suprisingly, the 1,3,4-thiadiazole derivatives according to the invention display a better herbicidal activity than the known imidazolidin-2-one-carboxylic acid isobutylamide which is chemically the nearest active compound of the same type of action. The compounds according to the invention thus represent an enrichment of the art.

R$^1$ is preferably straight-chain or branched alkyl of from 1 to 5 carbon atoms, especially of from 1 to 4 carbon atoms; straight-chain or branched alkenyl of from 3 to 5 carbon atoms, especially of from 3 to 4 carbon atoms; haloalkyl of from 1 or 2 carbon atoms and 2 to 5 halogen atoms, especially fluoroine; optionally substituted alkyl or aralkyl of from 6 to 10, especially 6, carbon atoms in the aryl part and 1 or 2 carbon atoms in the alkyl part (preferred substituents being straight-chain or branched alkyl of from 1 to 4 carbon atoms, haloalkyl of from 1 or 2 carbon atoms and 2 to 5 halogen atoms, especially fluorine, alkoxy of from 1 to 3 carbon atoms, halogen, especially chlorine, nitro and/or nitrile); alkylthio, alkylsulfonyl or alkylsulfoxyl, in each case of from 1 to 4 carbon atoms; or aralkylthio, aralkylsulfonyl or aralkylsulfoxyl, in each case of from 1 or 2 carbon atoms in the alkyl part and 6 to 10, expecially 6, carbon atoms in the aryl part.

The invention also provides a process for the production of a heterocyclic-substituted 1,3,4-thiadiazole derivative of formula (I) in which a 1,3,4-thiadiazolyl-(2)-urea of the general formula

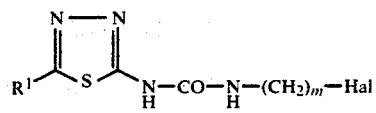

in which
R$^1$ has the abovementioned meaning,
m represents 2 or 3, and
Hal represents halogen, especially chlorine, is heated at 50°–120° C., in the presence of an acid-binding agent and optionally in the presence of a diluent, and the hexahydropyrimidin-2-one or imidazolidin-2-one thus produced, of the general formula

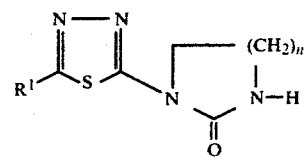

in which
R$^1$ and n have the abovementioned meanings, is reacted with an alkylating agent, for example dimethyl sulfate, diethyl sulfate, methyl iodide or ethyl iodide, in the presence of an acid-binding agent and optionally in the presence of a diluent, at temperatures of −5° to +100° C.

If 1-[5-trifluoromethyl-1,3,4-thiadiazolyl-(2)]-3-β-chloroethyl-urea and dimethyl sulfate are used as starting materials, the course of the reaction can be represented by the following formula scheme:

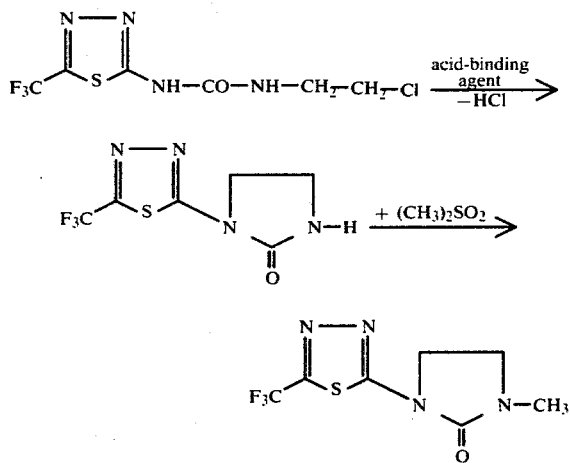

Formula (II) provides a general definition of the 1,3,4-thiadiazolyl-(2)-ureas which can be used as starting materials in the process of the invention. Some of their compounds are known (compare German Offenlegungsschrift (German Published Specification) 1,770,467 and Swiss Patent Specification 522,681). Those which are not known can be prepared according to processes described there (compare also the preparative Examples below).

The following may be mentioned as examples of the 1,3,4-thiadiazolyl-(2)-ureas:
  1-[5-tert.-butyl-1,3,4-thiadiazolyl-(2)]-3-β-chloroethylurea, 1-[5-tert.-butyl-1,3,4-thiadiazolyl-(2)]-3-γ-chloropropylurea,
1-[5-trifluoromethyl-1,3,4-thiadiazolyl-(2)]-3-γ-chloropropylurea,
1-[5-methylthio-1,3,4-thiadiazolyl-(2)]-3-β-chloroethylurea,
1-[5-ethylthio-1,3,4-thiadiazolyl-(2)]-3-β-chloroethylurea,
1-[5-methylthio-1,3,4-thiadiazolyl-(2)]-3-γ-chloropropylurea,
1-[5-ethylthio-1,3,4-thiadiazolyl-(2)]-3-γ-chloropropylurea,
1-[5-propylthio-1,3,4-thiadiazolyl-(2)]-3-β-chloroethylurea,
1-[5-propylthio-1,3,4-thiadiazolyl-(2)]-3-γ-chloropropylurea,
1-[5-butylthio-1,3,4-thiadiazolyl-(2)]-3-γ-chloropropylurea,
1-[5-butylthio-1,3,4-thiadiazolyl-(2)]-3-γ-chloroethylurea,
1-[5-sec.-butylthio-1,3,4-thiadiazolyl-(2)]-3-β-chloroethylurea,
1-[5-sec.-butylthio-1,3,4-thiadiazolyl-(2)]-3-γ-chloropropylurea,
1-[5-ethylsulfonyl-1,3,4-thiadiazolyl-(2)]-3-γ-chloroethylurea,
1-[5-acethylsulfonyl-1,3,4-thiadiazolyl-(2)]-3-γ-chloropropylurea,
1-[5-methylsulfonyl-1,3,4-thiadiazolyl-(2)]-3-γ-chloroethylurea,
1-[5-methylsulfonyl-1,3,4-thiadiazolyl-(2)]-3-γ-chloropropylurea,
1-[5-ethylsulfoxyl-1,3,4-thiadiazolyl-(2)]-3-γ-chloropropylurea,
1-[5-ethylsulfoxyl-1,3,4-thiadiazolyl-(2)]-3-γ-chloroethylurea,
1-[5-benzyl-1,3,4-thiadiazolyl-(2)]-3-β-chloroethylurea, 1-[5-phenyl-1,3,4-thiadiazolyl-(2)]-3-β-chloroethylurea,
1-[5-benzylmercapto-1,3,4-thiadiazolyl-(2)]-3-β-chloroethylurea,
1-[5-benzylmercapto-1,3,4-thiadiazolyl-(2)]-3-γ-chloropropylurea,
1-[5-benzylsulfonyl-1,3,4-thiadiazolyl-2(2)]-3-γ-chloropropylurea,
1-[5-benzylsulfoxyl-1,3,4-thiadiazolyl-(2)]-3-γ-chloropropylurea,
1-[5-benzylsulfonyl-1,3,4-thiadiazolyl-(2)]-3-β-chloroethylurea; and
1-[5-benzylsulfoxyl-1,3,4-thiadiazolyl-(2)]-3-β-chloroethylurea.

Polar solvents can be used as diluents in the reaction according to the invention to give the imidazolidiones or tetrahydropyrimidionones of formula (III). Preferred solvents include alcohols such as methanol, ethanol, propanol and butanol, nitriles such as acetonitrile, chlorinated hydrocarbons such as 2,4-dichlorobenzene, and/or water.

All customary acid-binding agents can be used as acid binders; alkali metal hydroxides, for example sodium hydroxide or potassium hydroxide, alkali metal carbonates, for example sodium carbonate or potassium carbonate, alkaline earth metal hydroxides, for example calcium hydroxide or magnesium hydroxide, and alkaline earth metal carbonates, for example calcium carbonate or magnesium carbonate, are preferred.

The reaction according to the invention to give imidazolidinones or tetrahydropyrimidinones of formula (III) can in general be carried out in a temperature range of 50° to 120° C., preferably of from 80° to 120° C.

In carrying out the preparation of compounds of formula (III), 1 to about 1.1 moles of acid-binder are generally employed per mole of the compounds of formula (II).

The compounds of formula (III) may be isolated as follows: the reaction mixture is hydrolyzed and the resulting precipitate is filtered off and optionally purified by recrystallization.

Polar organic solvents are also preferred as diluents in the reaction of the second stage of the process of the invention, which yields the compounds of formula (I). These solvents include halogenated hydrocarbons such as chloroform or methylene chloride, ethers such as diethyl ether, dibutyl ether, tetrahydrofuran or dioxan, and sulfoxides such as dimethylsulfoxide.

The acid-binding agents employed may be those already described in connection with the first stage of the process.

The alkylating agents used are generally dialkyl sulfates, such as dimethyl sulfate and diethyl sulfate, or alkyl halides such as methyl iodide, ethyl iodide or ethyl bromide.

The reaction according to the invention to give compounds of formula (I) is carried out in a temperature range of −5° to +100° C., preferably at 0° to 50° C.

About 1 mole of alkylating agent and 1 to 1.5 moles of acid binder are generally employed per mole of the compound of formula (III). Exceeding the stoichiometric ratios to a greater extent does not produce any substantial improvement in yield.

To isolate the compounds according to the invention of formula (I), the reaction mixture may be poured onto ice and the resulting precipitate filtered off and optionally purified by recrystallization.

The following examples are illustrative of the preparation of the instant compounds:

EXAMPLE 1

1-[5-trifluoromethyl-1,3,4-thiadiazolyl-(2)]-3-methyl-imidazolidin-2-one (a) First Stage

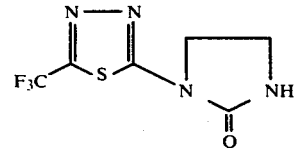

A mixture of 19.2 g (0.07 mole) of 1-[5-trifluoromethyl-1,3,4-thiadiazolyl-(2)]-3-β-chloroethylurea, 3.92 g (0.07 mole) of potassium hydroxide, 11.2 ml of water and 28 ml of ethanol was heated to the boil under reflux for 10 minutes. After cooling, the reaction mixture was poured into 200 ml of water and the resulting precipitate was filtered off, rinsed with ice water and dried.

Recrystallization from ethanol yielded 12.6 g (76% of theory) of 1-[5-trifluoromethyl-1,3,4-thiadiazolyl-(2)]-imidazolidin-2-one of melting point 198° C.

(b) Second stage

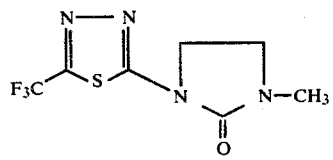

42.3 g (0.18 mole) of 1-[5-trifluoromethyl-1,3,4-thiadiazolyl-(2)]-imidazolidin-2-one were slowly added to a suspension of 11.9 g (0.213 mole) of powdered potassium hydroxide in 100 ml of dimethylsulfoxide. 25.2 g (0.18 mole) of methyl iodide were added dropwise thereto at an internal temperature of 5° to 10° C., while stirring and cooling externally.

After heating for two hours to 50° C., the reaction mixture was cooled and poured into 400 ml of water. The resulting precipitate was filtered off, washed with ice water, dried in vacuo and purified by recrystallization.

33.9 g (75% of theory) of 1-[5-trifluoromethyl-1,3,4-thiadiazolyl-(2)]-3-methyl-imidazolidin-2-one of melting point 176° C. (from ethyl acetate) were obtained.

EXAMPLE 2

1-[5-tert.-butyl-1,3,4-thiadiazolyl-(2)]-3-methyl-hexahydropyrimidin-2-one (a) First Stage

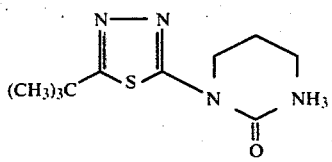

A mixture of 21.8 g (0.08 mole) of 1-[5-tert.-butyl-1,3,4-thiadiazolyl-(2)]-3-γ-chloropropylurea, 4.4 g (0.08 mole) of potassium hydroxide and 63 ml of ethanol was heated to the boil under reflux for 10 minutes. After cooling, the reaction mixture was poured into 400 ml of water and the resulting precipitate was filtered off, rinsed with water, dried and recrystallized from ethyl acetate.

17 g (89% of theory) of 1-[5-tert.-butyl-1,3,4-thiadiazolyl-(2)]-hexahydropyrimidin-2-one of melting point 187° C. were obtained.

(b) Second stage

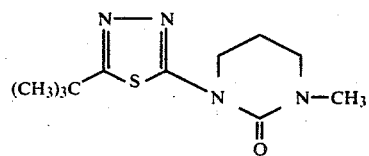

25.5 g (0.106 mole) of 1-[5-tert.-butyl-1,3,4-thiadiazolyl-(2)]-hexahydropyrimidin-2-one were slowly added to a suspension of 7.13 g (0.13 mole) of powdered potassium hydroxide in 65 ml of dimethylsulfoxide. 15.1 g (0.106 mole) of methyl iodide were slowly added dropwise thereto at an internal temperature of 5° to 10° C., while stirring and cooling.

After heating for two hours to 50° C. while stirring, the reaction mixture was cooled and poured into 300 ml of water. The resulting precipitate was filtered off, rinsed with water, dried in vacuo and recrystallized from ligroin/ethyl acetate.

21.5 g (80% of theory) of 1-[5-tert.-butyl-1,3,4-thiadiazolyl-(2)]-3-methyl-hexahydropyrimidin-2-one of melting point 100° C. were obtained.

EXAMPLES 3–16

The compounds of formula (I) identified in Table 2 below were prepared analogously to Examples 1 and 2, each being prepared in two stages (a) and (b).

First, the compounds of general formula (III), listed in Table 1 below, were prepared analogously to Examples 1(a) and 2(a):

TABLE 1

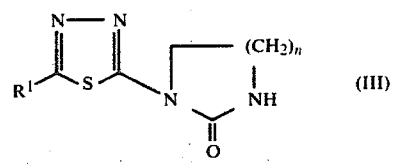

| | $R^1$ | n | Melting point (°C.) |
|---|---|---|---|
| 3(a) | $C(CH_3)_3$ | 1 | 205 |
| 6(a) | $CF_3$ | 2 | 228 |
| 9(a) | $CH_3S$ | 1 | 180 |
| 10(a) | $C_2H_5S$ | 1 | 176 |
| 11(a) | $C_2H_5S$ | 2 | 133 |
| 13(a) | $n\text{-}C_3H_7S$ | 1 | 115 |
| 14(a) | $sec.C_4H_9S$ | 1 | 107 |
| 15(a) | $C_2H_5SO_2$ | 1 | 175 |
| 16(a) | $C_2H_5SO_2$ | 2 | 217 |

Then the active compounds of general formula (I), listed in Table 2 below, were prepared analogously to Examples 1(b) and 2(b):

TABLE 2

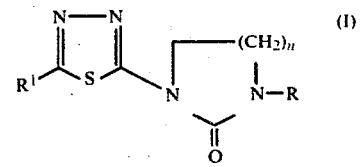

| | $R^1$ | $R^2$ | n | Melting point (°C.) |
|---|---|---|---|---|
| 3(b) | $C(CH_3)_3$ | $CH_3$ | 1 | 129 |
| 4(b) | $C(CH_3)_3$ | $C_2H_5$ | 1 | 75 |
| 5(b) | $C(CH_3)_3$ | $C_2H_5$ | 2 | 81 |
| 6(b) | $CF_3$ | $CH_3$ | 2 | 141 |
| 7(b) | $CF_3$ | $C_2H_5$ | 1 | 103 |
| 8(b) | $CF_3$ | $C_2H_5$ | 2 | 66 |
| 9(b) | $CH_3S$ | $CH_3$ | 1 | 125 |
| 10(b) | $C_2H_5S$ | $CH_3$ | 1 | 100 |
| 11(b) | $C_2H_5S$ | $CH_3$ | 2 | 62 |
| 12(b) | $C_2H_5S$ | $C_2H_5$ | 2 | 60 |
| 13(b) | $n\text{-}C_3H_7S$ | $CH_3$ | 1 | 101 |
| 14(b) | $sec.\text{-}C_4H_9S$ | $CH_3$ | 1 | 80 |
| 15(b) | $C_2H_5SO_2$ | $CH_3$ | 1 | 131 |
| 16(b) | $C_2H_5SO_2$ | $CH_3$ | 2 | 150 |

The preparation of the starting materials of formula (II) is exemplified below:

EXAMPLE (1)

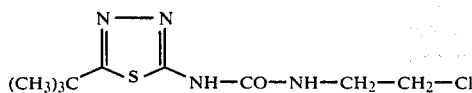

23.5 g (0.15 mole) of 2-amino-5-tert.-butyl-1,3,4-thiadiazol (prepared according to Bulletin de la Societe Chimique de France 1959, pages 477–479) were suspended in 200 ml of anhydrous ethyl acetate. 15.8 g (0.15 mole) of chloroethylisocyanate were added dropwise to this suspension at 40° C. internal temperature, with stirring and reflux cooling. In the course of the addition, the temperature gradually rose to 45° C.

After stirring for ten hours at 40°–45° C., the reaction mixture was filtered hot and the solvent was distilled off in vacuo. The solid which remained was recrystallized from 70 ml of ethyl acetate.

32.8 g (83.5% of theory) of 1-[5-tert.-butyl-1,3,4-thiadiazolyl-(2)]-3-$\beta$-chloroethylurea of melting point 131° C. were obtained.

The compounds of Table 3 below were prepared analogously:

TABLE 3

$$\underset{R^1}{\overset{N-N}{\underset{S}{\bigwedge}}}NH-CO-NH-(CH_2)_m-Cl \quad (II)$$

| Example No. | $R^1$ | m | Melting point (°C.) |
|---|---|---|---|
| (2) | C(CH$_3$)$_3$ | 3 | 97 |
| (3) | CF$_3$ | 2 | 128 |
| (4) | CF$_3$ | 3 | 137 |
| (5) | CH$_3$S | 2 | 170 |
| (6) | C$_2$H$_5$S | 2 | 162 |
| (7) | C$_2$H$_5$S | 3 | 128 |
| (8) | C$_3$H$_7$S | 2 | 144 |
| (9) | sec.C$_4$H$_9$S | 2 | 140 |
| (10) | C$_2$H$_5$SO$_2$ | 2 | 165 |

Further 2-amino-5-substituted 1,3,4-thiadiazoles can be prepared in accordance with the information in the following literature:

(1) Ber. dtsch. chem. Ges. 29, 2511 (1896)
(2) J. Chem. Soc. (London) 79, 54 (1901)
(3) U.S. Pat. No. 2,422,050, C.A. 41, 59021 (1947)
(4) Helv. Chim. Act. 33, 1353 (1950)
(5) U.S. Pat. No. 2,524,729, C.A. 45, 2030 (1951)
(6) Can. J. Chem. 37, 1121 (1959)
(7) JA Pat. No. 20,944–66, C.A. 66, 46430 f (1967)
(8) Arch. Pharm. 284, (1951), page 61
(9) J. of Het. Chem. 3. page 336 (1966)
(10) Farmaco Ed. Sci. 18 (8), pages 607–613 (1963)
U.S. Pat. No. 2,799,683 of July 16, 1957 (Messrs. American Cyanamid)
(12) U.S. Pat. No. 2,947,825 of Feb. 14, 1950 (Messrs. Monsanto)
(13) Pharmazeutische Zentralhalle, volume 107, issue 9 (1968), pages 656–657
(14) Zeitschrift fur Chemie 9 (1969) 12, 450.

The active compounds according to the invention are distinguished by a high herbicidal potency. They can therefore be employed with good success for destroying weeds.

Weeds in the broadest sense are plants which grow in places where they are not desired. As weeds, there may be mentioned: dicotyledons such as mustard (Sinapis), cress (Lepidium), cleavers (Galium), chickweed (Stellaria), camomile (Matricaria), gallant soldier (Galinsoga), goosefoot (Chenopodium), annual nettle (Urtica) and groundsel (Senecio), and monocotyledons such as timothy (Phleum), bluegrass (Poa), fescue (Festuca), goosegrass (Eleusine), foxtail (Setaria), ryegrass (Lolium) and barnyard grass (Echinochloa).

The active compounds according to the invention are in particular outstandingly suitable for combating grasses such as species of Echinochloa or Lolium. Furthermore, they can also be employed with particular advantage as selective agents for combating weeds, especially, for example, in crops of cereals or cotton. When used in larger amounts, they are also suitable as total herbicides.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents, and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, e.g. aerosol propellants, such as halogenated hydrocarbons, e.g. freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin, sulfite waste liquors and methyl cellulose.

The active compounds according to the invention can be used as a mixture with other active compounds.

The formulations in general contain from 0.1 to 95 percent by weight of active compound, preferably 0.5 to 90 percent by weight.

The active compounds can be employed as such or in the form of their formulations or the application forms prepared therefrom, such as ready-to-use solutions, emulsions, suspensions, powders, pastes and granules. They may be applied in the usual manner, for example by watering, spraying, atomizing, scattering or dusting.

They can be used either according to the post-emergence method or according to the pre-emergence method; when the active compounds are used as total herbicides, they are preferably applied after emergence of the plants, while when they are used as selective agents they are preferably applied before emergence. The amount of active compound employed can vary within substantial ranges. It depends essentially on the nature of the desired effect. In general, the amounts applied are from 0.1 to 25 kg/ha, preferably 0.5 to 10 kg/ha.

The invention therefore provides a herbicidal composition containing as active ingredient a compound according to the invention in admixture with a solid or liquefied gaseous diluent or carrier or in admixture with a liquid diluent or carrier containing a surface-active agent.

The invention also provides a method of combating weeds which comprises applying to the weeds or their habitat a compound according to the invention alone or in the form of a composition containing as active ingredient a compound according to the invention in admixture with a diluent or carrier.

The invention also provides crops protected from damage by weeds by being grown in areas in which, immediately prior to and/or during the time of the growing, a compound according to the invention was applied alone or in admixture with a diluent or carrier. It will be seen that the usual methods of providing a harvested crop may be improved by the present invention.

The compounds according to the invention, and the preparation and use of the compounds according to the invention, are illustrated by the following Examples.

EXAMPLE A

Post-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in the table. Depending on the concentration of the spray liquor, the amount of water used was between 1,000 and 2,000 liters per hectare. After three weeks, the degree of damage to the plants was determined and characterized by the values 0–5, which have the following meaning:

0 no effect
1 a few slightly burnt spots
2 marked damage to leaves
3 some leaves and parts of stalks partially dead
4 plant partially destroyed 5 plant completely dead The active compounds, the amounts used and the results can be seen from Table A.

Table A

| Active compound | Amount of active compound used, kg/ha | Post-emergence test | | | | | | | | |
|---|---|---|---|---|---|---|---|---|---|---|
| | | Echino-chloa | Cheno-podium | Sina pis | Galin-soga | Stell-aria | Urtica | Matri-caria | Cot-ton | Wheat |
| (CH₃)₃C—C(=N-N=)S—C—N(piperidine)—C(=O)—N—CH₃ (2) | 1 | 4–5 | 5 | 5 | 5 | 5 | 5 | 4 | 4 | 4 |
| | 0.5 | 4–5 | 5 | 5 | 5 | 5 | 5 | 3 | 3 | 3 |
| C₂H₅SO₂—C(=N-N=)S—C—N(piperidine)—C(=O)—N—CH₃ (16) | 1 | 5 | 5 | 5 | 5 | 5 | 5 | 5 | 4–5 | 2 |
| | 0.5 | 5 | 5 | 5 | 5 | 5 | 5 | 5 | 4 | 1 |
| CF₃—C(=N-N=)S—C—N(piperidine)—C(=O)—N—CH₃ (6) | 1 | 5 | 5 | 5 | 5 | 5 | 5 | 5 | 1 | 1 |
| | 0.5 | 4–5 | 5 | 5 | 5 | 5 | 5 | 4 | 0 | 0 |
| HN(CO)N—CO—NH—CH₂—CH(CH₃)₂ (known) | 1 | 0 | 2 | 2 | 2 | 1 | 3 | 2 | 1 | 0 |
| | 0.5 | 0 | 0 | 2 | 1 | 0 | 3 | 1 | 0 | 0 |

EXAMPLE B

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined and characterized by the values 0–5, which have the following meaning:

0 no effect
1 slight damage or delay in growth
2 marked damage or inhibition of growth
3 heavy damage and only deficient development or only 50% emerged
4 plants partially destroyed after germination or only 25% emerged
5 plants completely dead or not emerged.

The active compounds, the amounts applied and the results obtained can be seen from Table B.

invention and that other embodiments within the spirit and scope of the invention will suggest themselves to those skilled in the art.

What is claimed is:

1. A compound selected from the group consisting of 1-[5-tert.-butyl-1,3,4-thiadiazolyl-(2)]-3-methylhexahydropyrimidin-2-one, 1-[5-trifluoromethyl-1,3,4-thiadiazolyl-(2)]-3-methylhexahydropyrimidin-2-one, and 1-[5-ethylsulfonyl-1,3,4-thiadiazolyl-(2)]-3-methylhexahydropyrimidin-2-one.

2. Thiadiazole compound as claimed in claim 1, designated 1-[5-tert.-butyl-1,3,4-thiadiazolyl-(2)]-3-methylhexahydropyrimidin-2-one.

3. Thiadiazole compound as claimed in claim 1, designated 1-[5-trifluoromethyl-1,3,4-thiadiazolyl-(2)]-3-methylhexahydropyrimidin-2-one.

4. Thiadiazole compound as claimed in claim 1, designated 1-[5-ethylsulfonyl-1,3,4-thiadiazolyl-(2)]-3-methylhexahydropyrimidin-2-one.

Table B

| Active compound | Amount of active compound used, kg/ha | Pre-emergence test | | | | | | | |
| --- | --- | --- | --- | --- | --- | --- | --- | --- | --- |
| | | Echinochloa | Chenopodium | Lolium | Galinsoga | Matricaria | Cotton | Wheat | Corn |
| (CH₃)₃C—C(=N—N)S—C=N—N(—CH₂CH₂CH₂—)N—CH₃, C=O (2) | 5 | 5 | 5 | 5 | 5 | 5 | 2 | 1 | 2 |
| | 2.5 | 4–5 | 5 | 5 | 5 | 5 | 0 | 0 | 0 |
| C₂H₅SO₂—C(=N—N)S—C=N—N(—CH₂CH₂CH₂—)N—CH₃, C=O (16) | 5 | 5 | 5 | 5 | 5 | 5 | 2 | 1 | 3 |
| | 2.5 | 4–5 | 5 | 4–5 | 5 | 5 | 0 | 0 | 3 |
| HN—C(=O)—N—CO—NH—CH₂—CH(CH₃)(CH₃) (known) | 5 | 3 | 5 | 3 | 5 | 5 | 0 | 2 | 2 |
| | 2.5 | 2 | 5 | 3 | 5 | 5 | 0 | 2 | 0 |

It will be understood that the specification and examples are illustrative but not limitative of the present

* * * * *

UNITED STATES PATENT AND TRADEMARK OFFICE
CERTIFICATE OF CORRECTION

PATENT NO. : 4,195,181
DATED : March 25, 1980
INVENTOR(S) : Carl Metzger et al

It is certified that error appears in the above-identified patent and that said Letters Patent are hereby corrected as shown below:

Column 2, line 45 in formula
"$(CH_3)_2SO_2$" should read --$(CH_3)_2SO_4$--

Column 3, line 31 "methylsulfonyl" should read --methylsulfoxyl--

Column 5, line 35 in the formula "$NH_3$" should read --$NH$--

Column 7, line 55 insert (number) --11-- before "U.S."

Column 10, line 4 "suibable" should read --suitable--

Column 10, line 22 "5" should start a new line

Signed and Sealed this

Twenty-sixth Day of August 1980

[SEAL]

Attest:

SIDNEY A. DIAMOND

Attesting Officer

Commissioner of Patents and Trademarks